United States Patent
Gaylord et al.

(10) Patent No.: US 6,542,668 B2
(45) Date of Patent: Apr. 1, 2003

(54) VERY-HIGH-TEMPERATURE-STABLE FIBER GRATING-BASED SENSOR

(75) Inventors: Thomas K. Gaylord, Atlanta, GA (US); Gregory D. VanWiggeren, Los Gatos, CA (US); Donald D. Davis, Duluth, GA (US); Elias N. Glytsis, Atlanta, GA (US); Emmanuel Anemogiannis, Atlanta, GA (US)

(73) Assignee: Georgia Tech Research Corp., Atlanta, GA (US)

( * ) Notice: Subject to any disclaimer, the term of this patent is extended or adjusted under 35 U.S.C. 154(b) by 0 days.

(21) Appl. No.: 09/848,925

(22) Filed: May 3, 2001

(65) Prior Publication Data

US 2001/0055445 A1 Dec. 27, 2001

Related U.S. Application Data

(60) Provisional application No. 60/201,447, filed on May 3, 2000.

(51) Int. Cl.$^7$ ................................................. G02B 6/34
(52) U.S. Cl. ........................................................ 385/37
(58) Field of Search ............................................ 385/37

(56) References Cited

U.S. PATENT DOCUMENTS

| | | | | |
|---|---|---|---|---|
| 5,641,956 A | * | 6/1997 | Vengsarkar et al. | ... 250/227.14 |
| 5,945,666 A | | 8/1999 | Kersey et al. | ......... 250/227.14 |
| 6,075,907 A | | 6/2000 | Krol | ............................. 385/12 |
| 6,125,225 A | * | 9/2000 | Dianov et al. | ............... 385/124 |
| 6,137,565 A | * | 10/2000 | Ecke et al. | ................. 356/35.5 |
| 6,169,831 B1 | * | 1/2001 | Adams et al. | ................ 385/37 |

OTHER PUBLICATIONS

"Very–high–temperature stable $CO_2$–laser–induced long period fibre gratings;" by D.D. Davis, T.K. Gaylord, E.N. Glytsis and S.C. Mettler, *Electronics Letters*, Apr. 29, 1999, vol. 35, No. 9, pp. 740–742.

"Long–period fibre grating fabrication with focused $CO_2$ laser pulses;" by D.D. Davis, T.K. Gaylord, E.N. Glytsis, S.G. Kosinski, S.C. Mettler and A.M. Vengsarkar, *Electronics Letters*, Feb. 5, 1998, vol. 34, No. 3, pp. 302–303.

"Axial rotation dependence of resonances in curved $CO_2$–laser–induced long–period fibre gratings;" by G.D. VanWiggeren, T.K Gaylord, D.D. Davis, E. Anemogiannis, B.D. Garrett, M.T. Braiwish and E.N. Glytsis, *Electronics Letters*, Aug. 3, 2000, vol. 36, No. 16, pp. 1354–1355.

(List continued on next page.)

*Primary Examiner*—Robert H. Kim
*Assistant Examiner*—Richard Kim
(74) *Attorney, Agent, or Firm*—Troutman Sanders LLP; Todd Deveau

(57) ABSTRACT

An apparatus for measuring environmental parameters comprising an optical fiber-based sensor having thermally-induced diffraction gratings therein which are stable at very high temperatures for many hours. The diffraction gratings are, preferably, formed in an optical fiber by exposure to light from an infrared laser and do not degrade at high temperatures. A system for measuring an environmental parameter includes an optical fiber-based sensor, a light source, and a detector. According to a method of measuring an environmental parameter, the optical fiber-based sensor is positioned within a high-temperature environment having a parameter desired for measurement. The light source directs light into the optical fiber-based sensor. The detector measures the differential diffraction of the light output from the optical fiber-based sensor and determines a value of the environmental parameter based, at least in part, upon a known correlation between the differential diffraction and the environmental parameter.

22 Claims, 5 Drawing Sheets

OTHER PUBLICATIONS

"Tuning, attenuating, and switching by controlled flexure of long–period fiber gratings;" by G.D. VanWiggeren, T.K. Gaylord, D.D. Davis, M.I. Braiwish, E.N. Glytsis and E. Anemogiannis, *Optics Letters*, Jan. 15, 2001, vol. 26, No. 2, pp. 61–63.

"$CO_2$ laser–induced long–period fibre gratings: spectral characteristics, cladding modes and polarisation independence;" by D.D. Davis, T.K. Gaylord, E.N. Glytsis and S.C. Mettler, *Electronics Letters*, Jul. 9, 1998, vol. 34, No. 14, pp. 1416–1417.

"Fiber Grating Sensors;" by Alan D. Kersey, Michael A. Davis, Heather J. Patrick, Michel LeBlanc, K.P. Koo, C.G. Askins, M.A. Putnam and E. Joseph Friebele; *Journal of Lighwave Technology*, vol. 15, Aug. 1997, pp. 1442–1463.

"Simultaneous strain and temperature measurement with long–period gratings;" by Vikram Bhatia, David Campbell, Richard O. Claus and Ashish M. Vengsarkar; *Optics letters*, May 1, 1997, vol. 22, No. 9, pp. 648–650.

"Optical fiber long–period grating sensors;" by Vikram Bhatia and Ashish M. Vengsarkar; *Optics letters*, May 1, 1996, Vo91. 21, No. 9, pp. 692–694.

"Experimental Demonstration of a Fiber Bragg Grating Accelerometer;" by T.A. Berkoff and A.D. Kersey; *IEEE Photonics Technology Letters*, Dec. 1996, vol. 8, No. 12, pp. 1677–1679.

"Displacements of the resonant peaks of a long–period fiber grating induced by a change of ambient refractive index;" by Byeong Ha Lee, Yu Liu, Sang Bae Lee, Sang Sam Choi and Joo Nyung Jang; *Optics Letters*, Dec. 1, 1997, vol. 22, No. 23, pp. 1769–1771.

"Hybrid Fiber Bragg Grating/Long Period Fiber Grating Sensor for Strain/Temperature Descrimination;" by H.J. Patrick, G.M. Williams, A.D. Kersey, J.R. Pedrazzani and A.M. Vengsarkar; *IEEE Photonics Technology Letters*, Sep. 1996, vol. 8, No. 9, pp. 1223–1225.

* cited by examiner

VERY-HIGH-TEMPERATURE-STABLE FIBER GRATING-BASED SENSOR

CROSS-REFERENCE TO RELATED APPLICATIONS

This application claims priority on U.S. Provisional Patent Application Ser. No. 60/201,447, filed May 3, 2000, now pending.

FIELD OF THE INVENTION

The present invention relates, generally, to optical fiber-based sensors and, more specifically, to very-high-temperature stable optical fiber-based sensors having internal gratings which differentially diffract light of different wavelengths in a manner related to an environmental parameter.

BACKGROUND OF THE INVENTION

In recent years, optical fiber-based sensors have become an increasingly accepted alternative to conventional sensing technologies. Optical fiber-based sensors have been developed which allow for highly sensitive measurement of environmental parameters such as temperature, pressure, strain, and chemical concentrations, while offering a high degree of resistance to electromagnetic interference. Also, optical fiber-based sensors may be imbedded in structures to allow in situ measurement of internal environmental parameters which would, otherwise, not be readily measurable. Fiber-based sensors offer many additional advantages over their pneumatic and electronic counterparts including: increased sensitivity, geometrical flexibility, ease of miniaturization, and multiplexing capabilities.

A number of optical fiber-based sensors have been developed to utilize these advantages. Prior optical fiber-based sensors have, generally, been fabricated by writing gratings into selected portions of the core of an optical fiber by exposing those portions to intensely focused light having a wavelength to which the optical fiber is photosensitive. The light photoinduces a refractive index variation onto the selected portions of the fiber to produce a diffraction grating. Two basic types of these gratings are typically employed and include long-period fiber gratings and short period fiber gratings. The long-period fiber gratings (LPFG's) have a periodicity or spacing of the gratings (50–1500 microns) along the fiber length that is much larger than the wavelength of light source used during operation of the optical fiber. This is in contrast to short-period gratings, also known as fiber Bragg gratings, which have periods that are, generally, less than the wavelength of the light source used during operation of the optical fiber. Optical fiber-based sensors which use short-period fiber Bragg gratings, typically, suffer from the disadvantage of having relatively low sensitivity in comparison to optical fiber-based sensors having long-period fiber gratings.

The most commonly used current method for producing optical fiber-based sensors relies on the use of ultraviolet (UV) radiation to change the local refractive index of a specially-selected photosensitive optical fiber (referred to herein as "UV-induced optical fiber gratings'). Germanosilicate glasses have been found to be especially well suited for the writing of gratings therein using UV radiation. Grating patterns are commonly written onto UV-sensitive optical fibers using KrF or ArF excimer lasers operating at respective wavelengths of 193 or 248 nm. Suggested writing mechanisms have included UV absorption by germanium-oxygen vacancy defect centers, stress relief, and densification of the glass. The efficiency of writing onto a UV-sensitive optical fiber may be increased by preloading the optical fiber with molecular hydrogen.

Unfortunately, UV-induced optical fiber gratings have been found to have a limited high-temperature operational lifetime. Further, UV-induced optical fiber gratings are known to degrade as a result of annealing at 300–400 degrees Celsius, and are substantially erased after less than an hour of such annealing. In fact, the degradation of UV-induced optical fiber gratings may be a problem even at room temperature, although pre-annealing may be used to stabilize their properties at room temperature over longer time periods. Such degradation has precluded the use of UV-induced optical fiber gratings in some hostile environments.

Thus, it appears that none of the prior art optical fiber-based sensors are ideally suited for use in hostile, high-temperature environments. Therefore, there exists a need in the industry for an optical fiber-based apparatus and method of measuring environmental parameters in high-temperature environments and a method for manufacturing an optical fiber-based sensor for use therein, which address these and other related, and unrelated, problems.

SUMMARY OF THE INVENTION

Broadly described, the present invention comprises an optical fiber-based apparatus, or system, for measuring an environmental parameter in a high-temperature environment, a method of using the optical fiber-based apparatus for such measurement, and a method of manufacturing the optical fiber-based apparatus. More particularly and in accordance with exemplary embodiments, the optical fiber-based apparatus comprises an optical fiber-based sensor including a silica-based optical fiber which has a plurality of thermally-induced, long-period fiber gratings disposed thereon at appropriate locations along the longitudinal axis of the optical fiber. The gratings exhibit exceptional thermal stability and do not degrade at temperatures in excess of 600 degrees Celsius or in excess of 1200 degrees Celsius, thereby enabling the optical fiber-based sensor of the present invention to be used for measuring environmental parameters such as temperature, pressure, strain, or chemical composition, in high-temperature environments.

The optical fiber-based apparatus further comprises a light source operatively coupled to one end of the optical fiber-based sensor and a detector operatively coupled to the other end thereof. Preferably, the light source includes tunable, monochromatic light source such as, for example and not limitation, a tunable carbon dioxide laser or tunable infrared laser. Also preferably, the detector includes a photodetector and associated circuitry appropriate for receiving light pulses, and measuring the transmission time of the received light pulses from the light source and the differential diffraction of received light pulses having different wavelengths. Additionally, the detector preferably includes a processor for relating the measured differential diffraction to an environmental parameter being measured based, at least in part, on a known correlation between the measured differential diffraction and the environmental parameter.

In accordance with a method of using the optical-fiber based apparatus, the optical fiber-based sensor is positioned within an environment for which an environmental parameter is to determined. Because the optical fiber-based sensor is relatively flexible, is highly sensitive, and is not effected by electromagnetic radiation, the sensor may be positioned in a wide variety of environments (including, high-temperature environments) and in many orientations, and may even be imbedded in a wall manufactured of a solid material such as metal or concrete. Once positioned, the ends of the optical fiber-based sensor are operatively coupled to the light source and to the detector. Then, to make a measurement of a desired environmental parameter, the wavelength differential diffraction of light pulses is measured by the light source sequentially producing and directing light pulses into the optical fiber-based sensor and by the detector ascertaining, in concert with the light source, the transmission time of the light pulses from the light source to the detector. Next, the detector determines the value of the environmental parameter being measured by relating the measured differential diffraction to the environmental parameter based, at least in part, on a known correlation between the differential diffraction in the grating and the environmental parameter.

The optical fiber-based sensor is, preferably, formed according to a method of manufacture which includes exposing a silica-based, single mode, optical fiber to pulses of light from an infrared laser at periodic intervals, or locations, along the fiber's length. Preferably, the light pulses of the infrared laser have a wavelength greater than approximately 2.0 $\mu$m above which silica glass generally absorbs. Upon exposure to the infrared light, the refractive indices of the exposed areas of the optical fiber are heated and are altered, thereby producing diffraction gratings which differentially diffract light of differing wavelengths. It is believed that the thermal heating of the optical fiber by the infrared laser causes local densification of the optical fiber material and/or stress relief which creates changes to the refractive indices of the exposed areas. Unlike diffraction gratings produced by the exposure of an optical fiber to ultraviolet light, the diffraction gratings produced by the thermal-inducement of the present invention are stable and do not degrade when used in high-temperature environments for long periods of time.

Accordingly, it is an object of the present invention to provide optical fiber-based sensors which are stable at high temperatures.

Another object of the present invention is to provide optical fiber-based sensors which are suitable for use in extreme environments.

Still another object of the present invention is to provide optical fiber-based sensors which are not subject to degradation over time due to room temperature annealing of gratings.

Still another object of the present invention is to provide a method of manufacturing optical fiber-based sensors utilizing relatively low cost silica-based optical fibers.

Other objects, features, and advantages of the present invention will become apparent upon reading and understanding the present specification when taken in conjunction with the appended drawings.

DETAILED DESCRIPTION OF THE EXEMPLARY EMBODIMENTS

Figure 1:
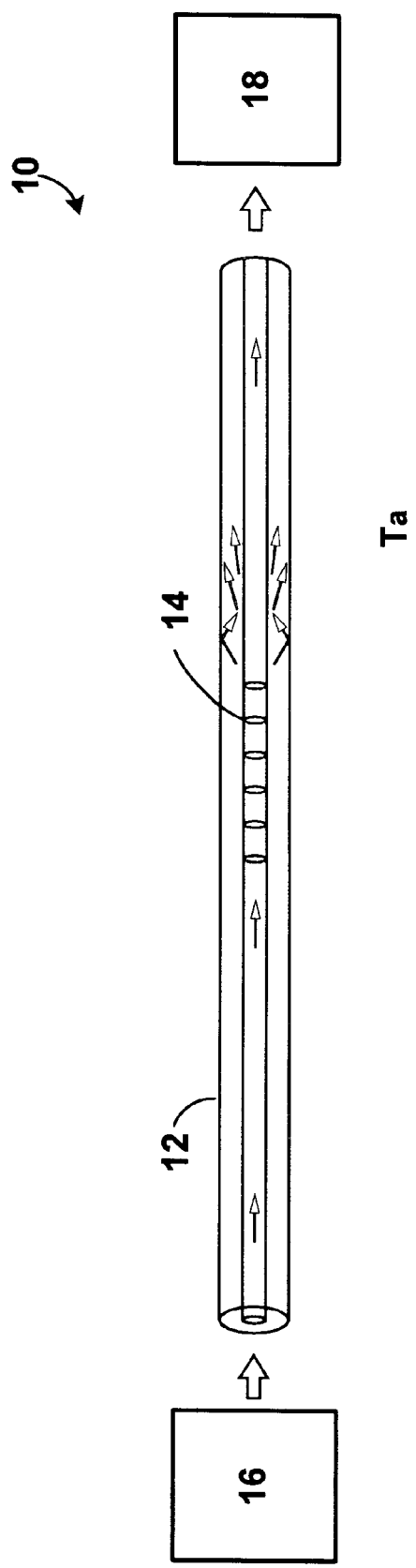
FIG. 1 is a block diagram representation of an optical fiber-based sensor system in accordance with a first exemplary embodiment of the present invention.

Referring now to the drawings in which the numerals represent like components or steps throughout the several views, FIG. 1 displays a block diagram representation of an optical fiber-based system 10 (also referred to herein as the "system 10") for measuring environmental parameters in high-temperature environments in accordance with a first exemplary embodiment of the present invention. As illustrated in FIG. 1, the system 10 includes an optical fiber-based sensor 12 having a plurality of diffraction gratings 14 disposed therein, a light source 16, and a detector 18. Preferably, the optical fiber-based sensor 12 is manufactured, according to a method of manufacture described below, from a silica-based optical fiber. Also preferably, the diffraction gratings 14 are thermally induced diffraction gratings formed according to the method of manufacture described below, and are thermally stable for use in high temperature environments having an ambient temperature (Ta) of at least 600 degrees Celsius and, more preferably, of at least 1200 degrees Celsius. The light source 16 is capable of producing and/or directing light having a wavelength commonly employed with optical fibers used for telecommunication applications. The detector 18 includes, preferably, a photodetector for receiving light and producing electrical output signals in response thereto. Detector 18 also, preferably, includes a processor for relating the measured differential diffraction to a desired environmental parameter, such as temperature, strain, pressure, or chemical composition, based at least upon a known correlation between the differential diffraction in the grating and the respective environmental parameter.

In operation, light source 16 directs light into the optical fiber-based sensor 12 wherein the light is differentially diffracted by diffraction gratings 14 in a manner dependent upon one or more environmental parameters. Detector 18 detects the differential diffraction of light within optical fiber-based sensor 12 and determines the value of the desired environmental parameter based, at least in part, upon the measured differential diffraction.

One of ordinary skill in the art should realize that a variety of light sources 16 and detectors 18 suitable for use in the current invention are commonly used in other optical fiber-based sensors and in telecommunication applications. In the first exemplary embodiment, light source 16 includes a tunable monochromatic light source, such as for example a tunable carbon dioxide laser or other tunable infrared laser. The wavelength differential diffraction of light pulses through fiber 12 is measured by sequentially applying light of various wavelengths and detecting the transmission time of the pulses using a simple photodetector as detector 18.

In a second exemplary embodiment substantially similar to the first exemplary embodiment, light source 16 instead includes a broadband light source. In order to measure the wavelength dependent differential diffraction of broadband light, detector 18 is adapted to function as a spectrum analyzer with the capability of simultaneously measuring the wavelength dependent transmission of light pulses at a plurality of different wavelengths. Additionally, one of ordinary skill in the art should recognize that other exemplary embodiments may exist, wherein the differential diffraction within the optical fiber-based sensor 12 is measured based on changes to transmission characteristics other than the travel time of light pulses.

According to an exemplary method of manufacturing an optical fiber-based sensor 12 having thermally-induced diffraction gratings 14 therein, an optical fiber is, preferably, exposed to infrared laser pulses at periodic intervals along the fiber's length as disclosed in Davis et al., *Long-period fiber grating fabrication with focused $CO_2$ laser pulses, Electronic Letters,* 34:302–303, 1999, herein incorporated by reference as if set forth in its entirety. As disclosed, the method is based on direct exposure of the fiber with 10.6 $\mu$m freespace wavelength carbon dioxide laser pulses which are in a portion of the infrared spectrum absorbed by the silica glasses from which optical fibers are commonly manufactured.

The optical fiber, is preferably, a silica-based fiber such as a single-mode optical fiber commonly used in telecommunication applications, although a multi-mode optical fiber may also be suitable. For example, optical fiber-based sensors 12 have been successfully fabricated by writing long-period fiber gratings 14 onto Corning SMF28, a widely used single-mode silica telecommunications fiber known to have a large tensile axial stress in its cladding. Gratings 14 have also been successfully written onto fibers available from other manufacturers, such as Lucent Technologies, according to the methods of the present invention.

Upon exposure to infrared laser radiation and heating, the refractive indices of the exposed areas of optical fiber are altered, effectively producing diffraction gratings 14 which differentially diffract light of differing wavelengths. It is believed that the change in refractive index of the exposed areas is due to local densification of the optical fiber material and/or stress relief as a result of thermal heating by the laser. Whatever the mechanism, the infrared laser-induced (i.e., thermally-induced) long-period fiber gratings 14 of the present invention are highly stable even when subjected to temperatures up to 1200 degrees Celsius for many hours. Thus, in contrast to UV-induced optical fiber gratings, the thermally-induced gratings 14 appear to be permanent and can operate in high-temperature environments for extended periods of time without degradation.

Preferably, the laser used to create the gratings 14 emits light the infrared portion of the spectrum (i.e., approximately 1.0 $\mu$m to 1000 $\mu$m) having a wavelength of greater than approximately 2.0 $\mu$m, above which silica glass generally absorbs. More preferably, the laser operates in the range of approximately 9.0 $\mu$m to approximately 11.0 $\mu$m, wherein carbon dioxide lasers and tunable carbon dioxide lasers typically operate. One of ordinary skill in the art should recognize that a variety of other lasers may be adapted to emit light in portions of the electromagnetic spectrum readily absorbed by silicate glass and that such lasers may also likely be effective to produce gratings according to the present invention. Such other types of lasers include, for example and not limitation, excimer lasers, semiconductor lasers, doped crystal lasers, liquid dye lasers and gas lasers which operate in the infrared portion of the electromagnetic spectrum. Additionally, other heating methods such as exposure of the fiber to electric arcs, ultrasound, microwave radiation, or electron beams may be suitable to heat selected optical fiber portions appropriately to produce gratings in accordance with the present invention.

When writing gratings onto the optical fiber of the optical fiber-based sensor 12 using an infrared laser, the optical fiber is not physically deformed and neither UV exposure nor hydrogen loading is required. However, hydrogen loading may enhance the writing sensitivity. Because there is no UV exposure or photoablation, the measured refractive index increases apparently occur through stress relief and/or densification of the optical fiber 12 due to localized heating, rather than through the mechanisms of 5 eV photoexcitation or material removal which are thought to be involved in UV-induced optical fiber grating formation in germanosilicate glasses.

Figure 2A:
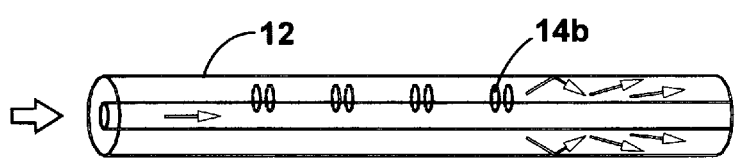
FIG. 2A is a pictorial representation of an optical fiber-based sensor having a long-period fiber grating.
Figure 2B:
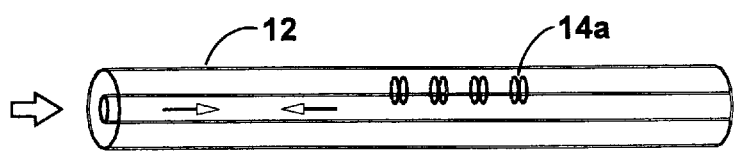
FIG. 2B is a pictorial representation of an optical fiber-based sensor having a short-period fiber grating.

The diffraction gratings 14 written onto the optical fiber of the optical fiber-based sensor 12 preferably include long-period fiber gratings (LPFGs) 14a having a period much longer than the wavelength of the light which is to be measured by the external detector equipment (see FIG. 2A). However, one of ordinary skill in the art should recognize that short-period fiber Bragg gratings 14b may also be written into an optical fiber in accordance with the methods of the present invention (see FIG. 2B).

More specifically, in accordance with the exemplary method of manufacture of the present invention the optical fibers are positioned in an alignment fixture using a computer-controlled translation stage. Under computer control, single laser pulses having an approximate energy of 0.5 W and a time duration of 300 ms) are focused onto a 140 mm diameter spot (~7.7 J/mm$^2$) at desired positions along the fiber's longitudinal axis. An optical imaging system mounted above the fiber aids in the alignment and enabled verification that no physical deformation is occurring. A broadband light source emitting light with a freespace wavelength in the range 1.4–1.6 $\mu$m and a spectrum analyzer are used to monitor the fiber transmission spectrum as the grating is written.

Figure 3:
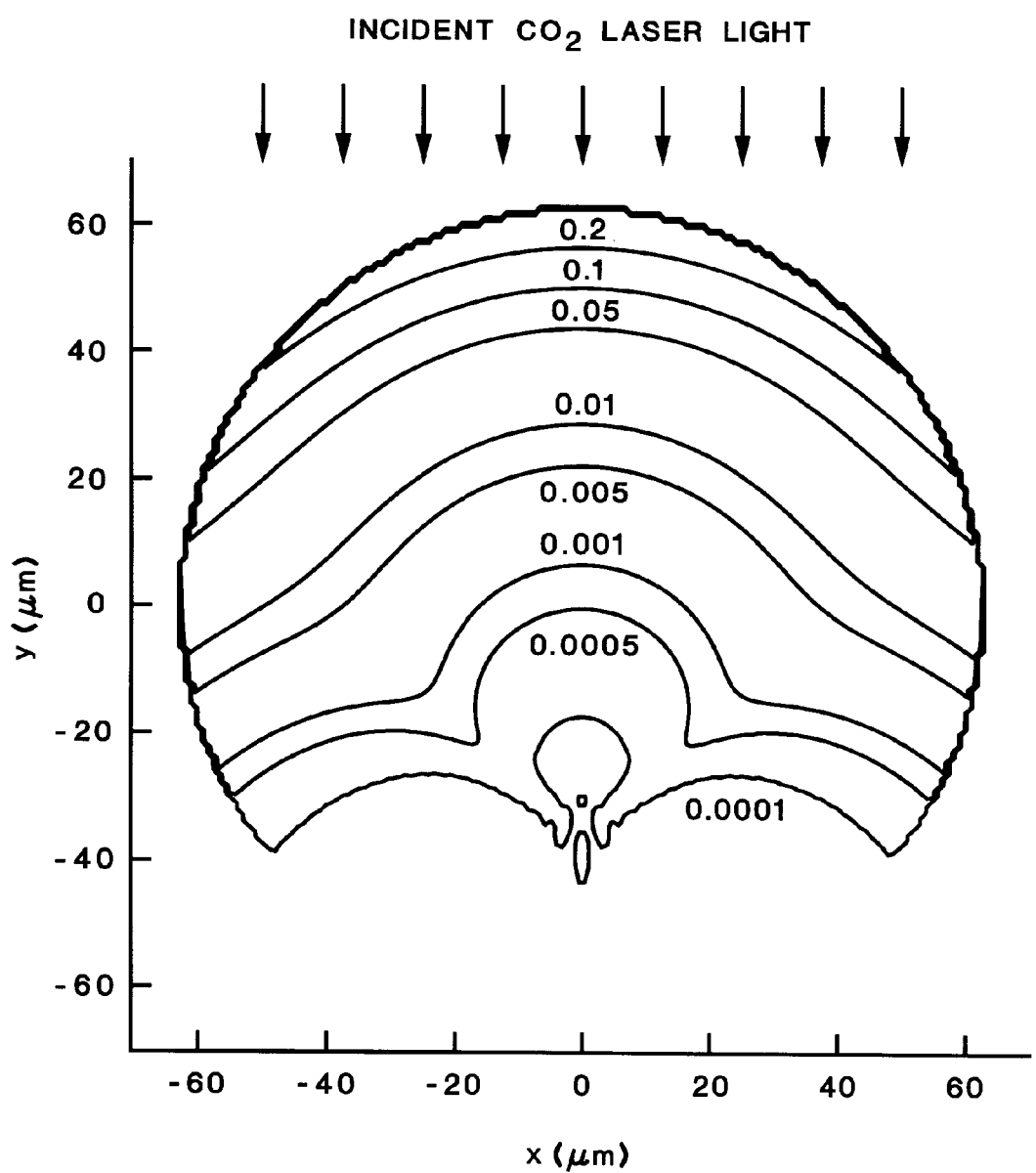
FIG. 3 is a cross-sectional view of the normalized intensity due to a transverse infrared beam being applied to the optical fiber-based sensor of FIG. 1.

The refractive index profiles written onto the optical fibers are measured by transverse interferometry. The transverse interferometric method, generally, assumes a radially symmetric fiber, which is not the case in the optical fiber-based sensors of the present invention due to the preferential heating of the optical fiber on only one side by the focused infrared laser beam. However, if the side of the optical fiber away from the laser pulse remains unperturbed, then the method yields an accurate profile for that side. On the perturbed side, an averaging of the refractive index occurs and the radial profile is substantially representative of the actual profile. The refractive index changes found in the cladding are consistent with the radially symmetric index changes found when the optical fiber was heated in a flame. The refractive index changes in the core of a hydrogen-loaded fiber are symmetric. FIG. 3 illustrates a cross-sectional view of the normalized intensity variations due to a transverse infrared beam applied to the fiber.

The period of the cladding refractive index corresponds to the writing period. The cladding refractive index maxima and the core refractive index maxima occur at locations where the focused laser beam was incident. However, smaller core refractive index peaks occur on either side of these primary peaks. The period of the index modulation in the core of a hydrogen-loaded fiber is half that of the writing period. In addition, the index modulation of the pedestal and depressed cladding regions is shifted in phase with respect to that of the cladding. These differences between the gratings give rise to the changes in the measured grating transmission spectra.

The changes in refractive index of the cladding of the non-hydrogen-loaded fiber are not due to UV photoexcitation, since there is no UV radiation present. The absorption of silica at 10.6 mm results in essentially all of the energy being converted into heat in the first 10–20 microns of the glass. Possible mechanisms for the refractive index increase are residual stress relief and densification of the glass. Refractive index elevation in the cladding of $\Delta=0.02\%$ corresponds to relief of 9.5 kg/mm$^2$ stresses. This is higher than the 1.0 kg/mm$^2$ measured. Densification of the glass has been previously observed in some UV written gratings, and this writing process may be accelerated by heating. Densification has been proposed as a mechanism for writing waveguide structures in bulk glass using an infrared laser at 810 nm. In the infrared-laser-written optical fiber gratings described in the present invention, both stress relief and densification are likely to be present.

The thermal stability of the optical fiber grating-based sensors 12 of the present invention is demonstrated in Davis et al., *Very-high-temperature stable CO2-laser-induced long-period fiber gratings, Electronics Letters*, 35:9, pp. 740–742 (1999), herein incorporated as if set forth in its entirety. To examine the effects of annealing on thermally-induced LPFGs 14, 'moderately modulated' gratings, produced in accordance with the methods described herein, were placed in a tube furnace and subjected to a series of annealing times and temperatures. The optical fibers were held in the furnace by fixing the fiber's ends outside the tube. No tension was applied during heating other than the weight of the fiber itself. In each case, the grating was heated and then allowed to cool to room temperature before the transmission spectrum was measured using a tunable laser source and power meter.

Figure 4:
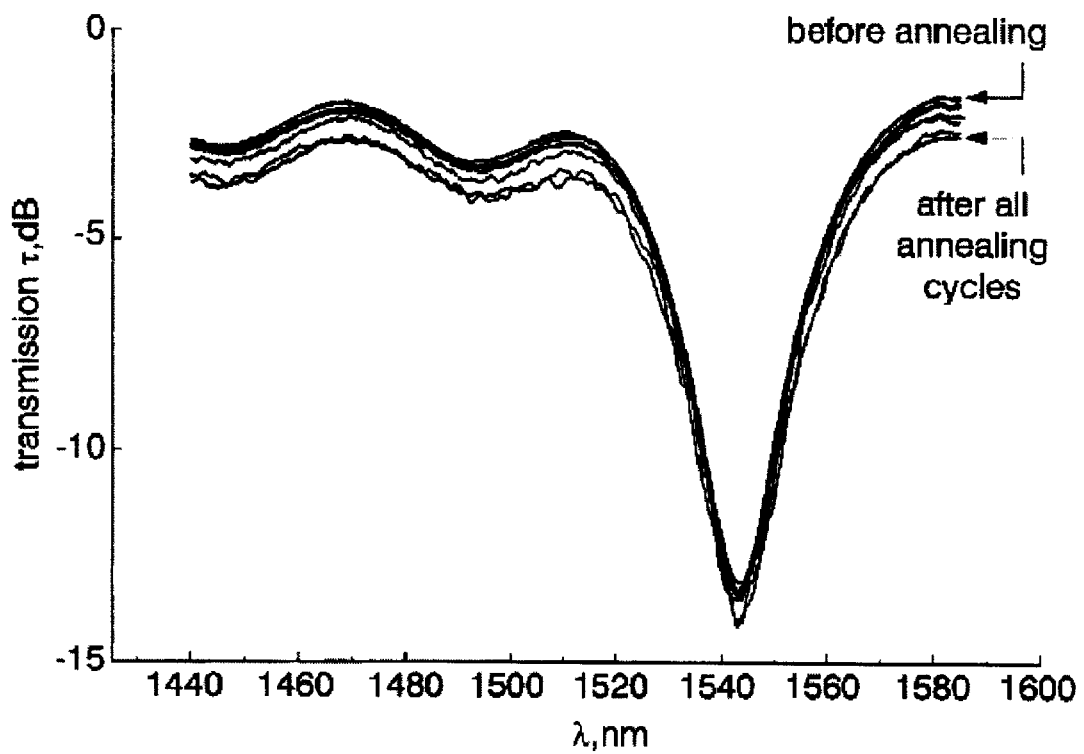
FIG. 4 is a graphical representation illustrating exemplary transmission spectra of thermally-induced long period fiber gratings, produced in accordance with a method of the present invention, after annealing at 600, 700, 800, 900, 1000, 1100, and 1200 degrees Celsius for one hour each and a final annealing at 1000 degrees Celsius for 24 hours.

The stability of thermally-induced gratings 14 is illustrated by the series of transmission spectra in FIG. 4. This grating was annealed for 1 hour at each temperature of 600, 700, 800, 900, 1000, 1100, and 1200 degrees Celsius. Following the 1200 degrees Celsius anneal cycle, the grating was further annealed for 24 hours at 1000° Celsius. Each cycle had a relatively rapid temperature rise (i.e. approximately 10 min), the indicated time at the specified temperature, and finally an exponential cooling to room temperature with a time constant of approximately 40 min. The strength of the resonant coupling showed no degradation after all of these annealing cycles. In this sample, the wavelength of resonant coupling was also stable.

Figure 5:
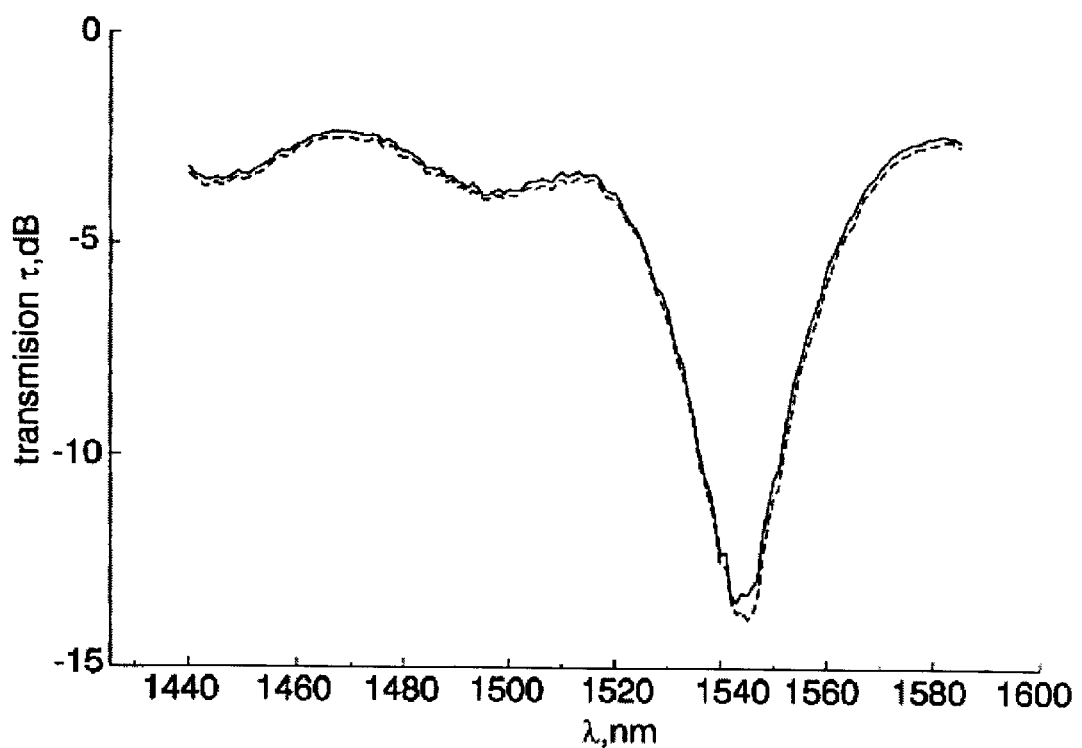
FIG. 5 is a graphical representation illustrating the polarization dependence of thermally-induced long period fiber gratings after multiple annealing cycles.

The polarization-dependent loss (PDL) of long-period fiber gratings 14a fabricated by infrared laser exposure in accordance with the method of the present invention is low, and is not degraded by the annealing process. FIG. 5 shows the PDL of the grating 14a of FIG. 4 after all of the annealing cycles were completed.

Thus, from FIGS. 4 and 5, it can be seen that optical fiber grating-based sensors 12 fabricated by exposure to infrared laser pulses are exceptionally stable. The optical fiber-based sensors 12 of the present invention exhibit band rejection characteristics that do not significantly change in resonant strength and resonant wavelength even when subjected to temperatures up to 1200° C. The gratings 14 of the sensor 12 are essentially permanent under high-temperature conditions wherein conventional UV-induced optical fiber gratings would be erased in seconds. Therefore, carbon dioxide laser-induced LPFGs are excellently suited for both long-lifetime and high-temperature applications.

The optical fiber-based sensors 12 of the present invention are usable according to the following method in order to determine the value of a desired environmental parameter. An optical fiber based sensor 12 having a plurality of diffraction gratings 14 disposed therein for differentially diffracting light in a manner dependent upon the desired environmental parameter is placed in a location wherein the desired environmental parameter is to be measured. Light from light source 16 is then directed through the optical fiber and the resultant wavelength dependent differential diffraction is measured by detector 18. The value of the environmental parameter is then determined based, at least in part, on the measured differential diffraction within the optical fiber and correlation therewith.

Whereas this invention has been described in detail with particular reference to its most preferred embodiment, it is understood that variations and modifications can be effected within the spirit and scope of the invention, as described herein before and as defined in the appended claims. The corresponding structures, materials, acts, and equivalents of all means plus function elements, if any, in the claims below are intended to include any structure, material, acts for performing the functions in combination with other claimed elements as specifically claimed.

What is claimed is:

1. A system for determining the value of an environmental parameter, said system comprising:

an optical fiber having a plurality of diffraction gratings disposed therein for differentially diffracting light in a manner dependent upon an environmental parameter, wherein at least some diffraction gratings of said plurality of diffraction gratings are formed by heating said optical fiber;

a light source for directing light into said optical fiber; and, a detector for detecting the differential diffraction of said light within said optical fiber and determining the value of said environmental parameter based at least in part on said detected differential diffraction;

wherein said plurality of diffraction gratings are stable at temperatures greater than 400 degrees Celsius.

2. The system of claim 1, wherein said plurality of diffraction gratings includes a plurality of long-period fiber gratings.

3. The system of claim 1, wherein said plurality of diffraction gratings includes a plurality of fiber Bragg gratings.

4. The system of claim 1, wherein said plurality of diffraction gratings include at least a fiber Bragg grating and a long-period fiber grating.

5. The system of claim 1, wherein at least some diffraction gratings of said plurality of diffraction gratings are formed using an infrared laser.

6. The system of claim 1, wherein at least some diffraction gratings of said plurality of diffraction gratings are formed using a laser adapted to emit light having a wavelength in the range of approximately 9 $\mu$m to 11 $\mu$m.

7. The system of claim 1, wherein at least some diffraction gratings of said plurality of gratings are formed using a carbon dioxide laser.

8. The system of claim 1, wherein said plurality of diffraction gratings are stable at temperatures greater than 600 degrees Celsius.

9. The system of claim 1, wherein said plurality of diffraction gratings are stable at temperatures greater than 1200 Celsius.

10. The system of claim 1, wherein said optical fiber is a silica-based fiber.

11. The system of claim 1, wherein said detector detects said differential diffraction by measuring the transmission time of light pulses within said optical fiber.

12. A method for determining the value of an environmental parameter comprising the steps of:
   directing light into an optical fiber having a plurality of diffraction gratings disposed therein for differentially diffracting light in a manner dependent upon an environmental parameter; and
   measuring the differential diffraction of said light within said optical fiber; and
   determining the value of said environmental parameter based at least in part on said measured differential diffraction;
   wherein said plurality of diffraction gratings are stable at temperatures greater than 400 degrees Celsius.

13. The method of claim 12, wherein at least some of said plurality of gratings are produced using an infrared laser.

14. The method of claim 12, wherein at least some of said plurality of gratings are produced using a laser having a wavelength in the range of approximately 9 $\mu$m to 11 $\mu$m.

15. The method of claim 12, wherein at least some of said plurality of gratings are produced using a carbon dioxide laser.

16. The method of claim 12, wherein said plurality of gratings are stable at temperatures greater than 600 degrees Celsius.

17. The method of claim 12, wherein said plurality of gratings are stable at temperatures greater than 1200 degrees Celsius.

18. The method of claim 12, wherein said gratings have been formed in said optical fiber by directing light from an infrared laser onto selected portions of said optical fiber, wherein said light has a wavelength in a portion of the spectrum absorbed by said optical fiber.

19. A method for manufacturing a fiber sensor useable for measuring an environmental parameter in a high temperature environment, the method comprising the steps of:
   providing an optical fiber; and,
   heating selected portions of said optical fiber to induce a plurality of diffraction gratings therein, wherein said diffraction gratings differentially diffract light in a manner dependent upon an environmental parameter, and wherein said diffraction gratings are stable at temperatures in excess of approximately 600 degrees Celsius.

20. The method of claim 19, wherein said step of heating includes a step of exposing said selected portions of said optical fiber to radiation from an infrared laser.

21. The method of claim 20, wherein said infrared laser emits light having a wavelength between 9 $\mu$m and 11 $\mu$m.

22. The method of claim 19, wherein said infrared laser includes a carbon dioxide laser.

* * * * *